United States Patent

Marsh et al.

[11] Patent Number: 5,844,123
[45] Date of Patent: Dec. 1, 1998

[54] GAS SENSING SYSTEM

[76] Inventors: Robert Anthony Marsh, Kingfisher House, 68 Pattison Lane, Woolstone, Milton Keynes, Buckinghamshire MK15 0ay; Rodney Edward Smith, Levant House, Little Chesterford, Saffron Walden, Essex CB10 1TS; Roger Kevin Starnes, 2 Balmoral Close, The Brackens Winsford, Cheshire CW7 2RS; John Wilfred Scarott, 53 Dickens Lane, Poynton, Stockport, Cheshire SK12 1NN; Colin Edwin Turner, 11 Stile Plantation, Royston, Hertfordshire, SG8 9HS, all of England

[21] Appl. No.: 750,285
[22] PCT Filed: May 30, 1995
[86] PCT No.: PCT/GB95/01243
§ 371 Date: Feb. 18, 1997
§ 102(e) Date: Feb. 18, 1997
[87] PCT Pub. No.: WO95/33202
PCT Pub. Date: Dec. 7, 1995

[30] Foreign Application Priority Data

Jun. 1, 1994 [DE] Germany .................. 94 10 950.1

[51] Int. Cl.$^6$ ............................................. G01N 1/22
[52] U.S. Cl. .................... 73/19.12; 73/31.07; 73/863.12
[58] Field of Search ............................ 73/19.05, 19.06, 73/19.1, 19.12, 31.07, 19.01, 803.11, 863.12

[56] References Cited

U.S. PATENT DOCUMENTS

| | | | |
|---|---|---|---|
| 4,073,619 | 2/1978 | Lawson | 73/863.11 |
| 4,517,135 | 5/1985 | Szerenyi et al. | 73/19.1 X |
| 4,550,590 | 11/1985 | Kesson | 73/19.05 |
| 5,144,831 | 9/1992 | Hale et al. | 73/19.05 |
| 5,255,553 | 10/1993 | Hale et al. | 73/19.1 |

*Primary Examiner*—Michael Brock

[57] ABSTRACT

A gas sensing system is provided for the detection of gas concentrations in a flowable medium. The gas sensing system has a gas permeable membrane structure to separate the flowable medium from a chamber where a gas sensor is positioned for detecting the gas concentration in the chamber. The sensor has predetermined environmental operating ranges and the system has a heat drain with a heat sink to maintain the temperature of gas in the chamber within the operating ranges, together with gas nozzles leading into the chamber to purge gas in the chamber and to maintain the gas concentration from exceeding the sensor operating range.

15 Claims, 5 Drawing Sheets

GAS SENSING SYSTEM

The present invention relates to a gas sensing system and was primarily developed for measuring gas concentrations, in solution, in gas mixtures, liquids and other fluid mediums, for example foodstuffs such as jams and other preserves, and for carrying out such measurements in-situ, preferably during the continuous flow of the medium. The system also has applications for gas sensing in other media, such as wine, beer, cider, sugar solutions, flowable solid material such as sugar, food granules and agglomerates together with non-foodstuffs such as pharmaceutical preparations and oils.

It is often important to know the concentrations of certain gases in certain mediums, and one of the most important applications is in determining the acceptability of foodstuffs. A prime example arises in the preserves industry where sulphur dioxide gas, $SO_2$, is frequently employed during storage and transportation as a preservative for the raw materials (for example, pulped fruit) from which the preserve is made. Once the preserve has been manufactured the sulphur dioxide may no longer be required in the finished product and, in fact, European Community Regulations are in force requiring that sulphur dioxide concentrations in preserves be less than thirty parts per million (ppm). In other foodstuffs and beverages (such as beer), legislation worldwide is becoming stricter and present U.S. requirements limit the $SO_2$ concentrations in beer to less than 10 ppm. However, in certain products such as wine, the sulphur dioxide is required, in known concentrations, to act as a preservative during storage. In both cases, it is highly desirable to know the concentration level of the sulphur dioxide.

The conventional procedure for regulating gas concentrations in preserves is by "boiling off" the gas by heating, or by vacuum processing the preserve sufficiently to cause the gas to evolve from solution until its concentration falls to a desired level. The conditions under which the boiling off procedure is effective will vary depending on the concentrations of the gas in the preserve and how it is chemically bound with the preserve (it is known that sulphur dioxide forms weak complexes with certain naturally occurring organic materials, particularly aldehydes and ketones, and such complexes are generally broken down at temperatures in excess of 60° C.) and therefore it is inevitable that the residual gas concentration in the finished product will vary.

Therefore, quality control checks are necessary at frequent intervals whereby samples of the preserve are taken and tested, using standard laboratory procedures, to determine the gas concentrations in the preserve product. In the production environment, known gas sensors are neither sufficiently rugged or suitable for use at the high temperatures and pressures generally required. Quality control regulations may require that certain gas concentrations, such as sulphur dioxide, in a foodstuff product may not exceed a permitted level. Furthermore, if following a quality control check on sulphur dioxide concentration it is found that the gas concentration level is too great, a continuous production line of the foodstuff may be stopped to determine the origin of the problem while the gas removal procedure is revised. Typically, the known method of gas concentration measurements (such as $SO_2$) is off-line, whereby a production sample is taken and gas concentration measurements are achieved by wet chemical means, a destructive test, taking between 30–60 minutes. During this period, production continues at the rate of several tonnes per hour. Therefore, if an unacceptable gas concentration is found then several tonnes of the product will have been produced which will be suspect and require further processing. Furthermore, simply increasing the boiling off time of the preserve to ensure that more gas will be removed, without control, would likely result in an unacceptable increase in production costs.

In addition, existing tests, even using the most accurate commercially available wet chemical testing methods (which take 40 minutes), result in test results showing a standard deviation of about 4 ppm when repeated measurements are taken of the same commercial sample having a concentration in the region off 10 ppm. Such a wide fluctuation of data from the test results where extremely small quantities are involved is detrimental to overall manufacturing capabilities, the risk existing that incorrect measurements (due simply to lack of measurement accuracy) could result is unacceptable product being declared acceptable and acceptable product being re-processed.

It is an object of the present invention to provide a gas sensing system which alleviates the aforementioned problems and enables gas concentration measurements to be carried out in-situ.

According to the present invention there is provided a gas sensing system for the detection of gas concentrations emanating from a flowable medium which comprises a membrane structure permeable to said gas and disposed between said flowable medium and a chamber, said membrane structure being impervious to said flowable material; a gas sensor exposed to said chamber for the detection of concentrations of said gas therein, said gas sensor having predetermined environmental operating ranges and wherein means is provided in said chamber whereby the physical characteristics of the gas in the chamber are controlled for the characteristics of the gas exposed to said sensor to be compatible with the predetermined operating ranges of the sensor. Such a system allows gas concentration measurements to be carried out on the medium in situ, enabling continuous testing of the medium which allows for greater process and quality control and provides the opportunity to blend separate batches of the medium.

Conventional gas sensors may have an operational temperature limitation less than a predetermined temperature and with such sensors a temperature control means may be provided, preferably within the chamber, for withdrawing heat from the chamber and the gas that enters the chamber through the membrane structure, thereby reducing the temperature of the gas within the chamber that is presented to the sensor to below the predetermined temperature. Preferably, the temperature control means comprises a heat sink such as a thermally conductive member through which heat from the chamber is conducted to a heat sink outside of the chamber. Usually, conduction means will also be employed to control the temperature of the sensor below the predetermined temperature, by conducting heat away from the gas sensing system, preferably such conducting means incorporating a heat sink. The use of such temperature control means also alleviates heat transfer through the gas sensing system to the sensor by conduction, thereby helping reduce the heating of the gas sensor beyond its operating range as a result of such heat conduction through the system.

Alternatively, or in addition, conventional gas sensors may have an operational gas concentration detection limitation which is less than a predetermined concentration for such sensors to provide increased detection accuracy or a high sensitivity. With such sensors purging means may be provided to reduce the concentration of gas within the chamber, as necessary, to maintain that gas concentration in the chamber below the predetermined concentration. Preferably, the chamber is sealed and the purging means may comprise inlet and outlet ports, an input port permitting the controlled introduction of a purging gas into the chamber and an outlet port permitting the mixed gaseous contents of the chamber to be removed from the chamber so that said chamber is filled with the purging gas.

Preferably, the system will comprise a pH sensor for detecting the pH level of the flowable medium. Typically, the pH sensor will be a pH Ion Sensitive Field Effect Transistor and such sensors advantageously serve to provide an accurate pH reading of the medium, which readings may be important in determining the actual gas concentrations in solution within the medium from the gas sensor reading, since the gas concentrations emanating from the medium may be proportional to the pH level of the medium.

In a preferred form of the present invention the system further comprises pressure detection means for determining the pressure of the flowable medium and a temperature detection means for determining the temperature of the flowable medium, either or both of which may advantageously serve in determining the physical state of the medium, basically its temperature and pressure, which may be important in determining the actual gas concentration in solution within the medium from the gas sensor reading, since the gas concentrations emanating from the medium may be proportional to the pressure and/or the temperature of the medium. In the case of $SO_2$ in preserves, for temperatures below 85° C. there is a significant temperature dependence of the gas concentration emanating from the medium. Above this temperature of 85° C. the complexes formed between the $SO_2$ and the organic materials are broken. This temperature dependency is also dependant on the organic material (and thus the complexes formed therewith) and is, for example, different for $SO_2$ in wine or $SO_2$ in beer. Above this complexation temperature test results have shown that the concentration of $SO_2$ emanating from preserves also varies with pressure variations and with variations of the preserve pH level as well as with further temperature variations.

The release of gas in solution in a medium is proportional to the physical characteristics of the medium, particularly temperature and pressure, and variations of these parameters will cause a variation of the concentration of gas released. By measuring the gas concentrations emanating from a medium and knowing the physical characteristics of the medium it is possible to determine the actual concentration of the gas in solution in the medium.

Typically, the flowable medium will flow through a pipe, in a wall of which is situated the membrane structure, so that a side face of the membrane structure is directed inwards towards a central axis of the pipe and usually it will be in contact with the medium. The membrane structure may be supported by a lattice frame to increase its mechanical strength. This membrane structure may comprise a single layer or a multiplicity of two or more layers.

The gas sensor may be of conventional structure and have a second gas permeable membrane structure disposed between the gas detection components of the sensor and the chamber.

The gas sensing system is preferably intended for detection of gas concentrations in solution in a non-gaseous flowable medium which will typically be liquid, paste, gel, powder or granules.

Further according to the present invention there is provided a method of determining concentration of a gas emanating from a flowable medium by use of a gas sensor having predetermined environmental operating ranges, comprising the steps of separating and isolating the said gas from the flowable medium and controlling the physical characteristics of the said isolated gas for said gas to be presented to the gas sensor in a condition in which its physical characteristics are compatible with the predetermined operating ranges of the gas sensor.

Usually, the gas will be separated from the flowable medium by location of a membrane structure, which is permeable to the gas and impermeable to the flowable medium, between said flowable medium and a chamber and allowing the gas to diffuse into the chamber for detection therein by the gas sensor.

The sensor used may have an operational temperature limitation less than a predetermined temperature and in such case when the gas emanating from a hot medium is at a temperature greater than the predetermined temperature, by the method of this invention heat may be withdrawn from the gas in the chamber to reduce the temperature of that gas to below the predetermined temperature for its exposure to the gas sensor, thereby adjusting the temperature of the gas to within the operating ranges of the sensor. As a further example, the sensor may have an operational concentration detection limitation less than a predetermined concentration and in such a case when the gas emanating from a medium is at a concentration greater than the predetermined concentration, by the method of this invention the concentration of the gas in the chamber may be controlled and prevented from reaching the predetermined concentration for its exposure to the gas sensor.

Primarily developed for sulphur dioxide concentration detection in preserves such as jam etc., it will be appreciated that this invention can also be applied to a large number of other situations, for example sulphur dioxide in wine production, where it is necessary to determine a gas concentration in solution (not necessarily sulphur dioxide) of a flowable medium.

In addition, it will also be appreciated that, optionally, the determining of the gas concentrations in solution of a flowable medium in accordance with the present invention can be carried out with the medium in a static state or when it is flowing.

An embodiment of a gas sensing system constructed in accordance with the present invention will now be described, by way of example only, with reference to the accompanying illustrative drawings in which.

Figure 3:
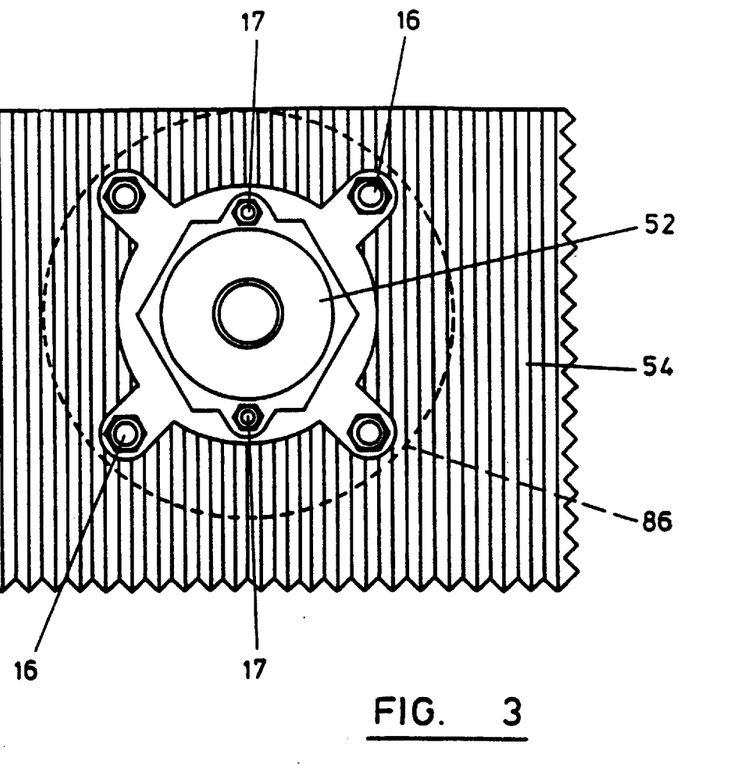
FIG. 3 is a plan view from above of the gas sensing unit of FIG. 1.

A gas sensing system 10 (FIG. 5) comprises a gas sensing unit 12 (FIG. 1), connected to a mounting block 13 by bolts 16 and 17 (FIG. 3), with this mounting block 13 surrounding and clamped onto an aluminium pipe 14, a pressure transducer 18 for determining pressure within the pipe 14 and a pH sensor head 20 for determining the pH level of the contents of the pipe 14. A longitudinal array of conventional thermocouples (not shown) are disposed within the pipe 14 for determining the temperature of the pipe contents.

Figure 5:
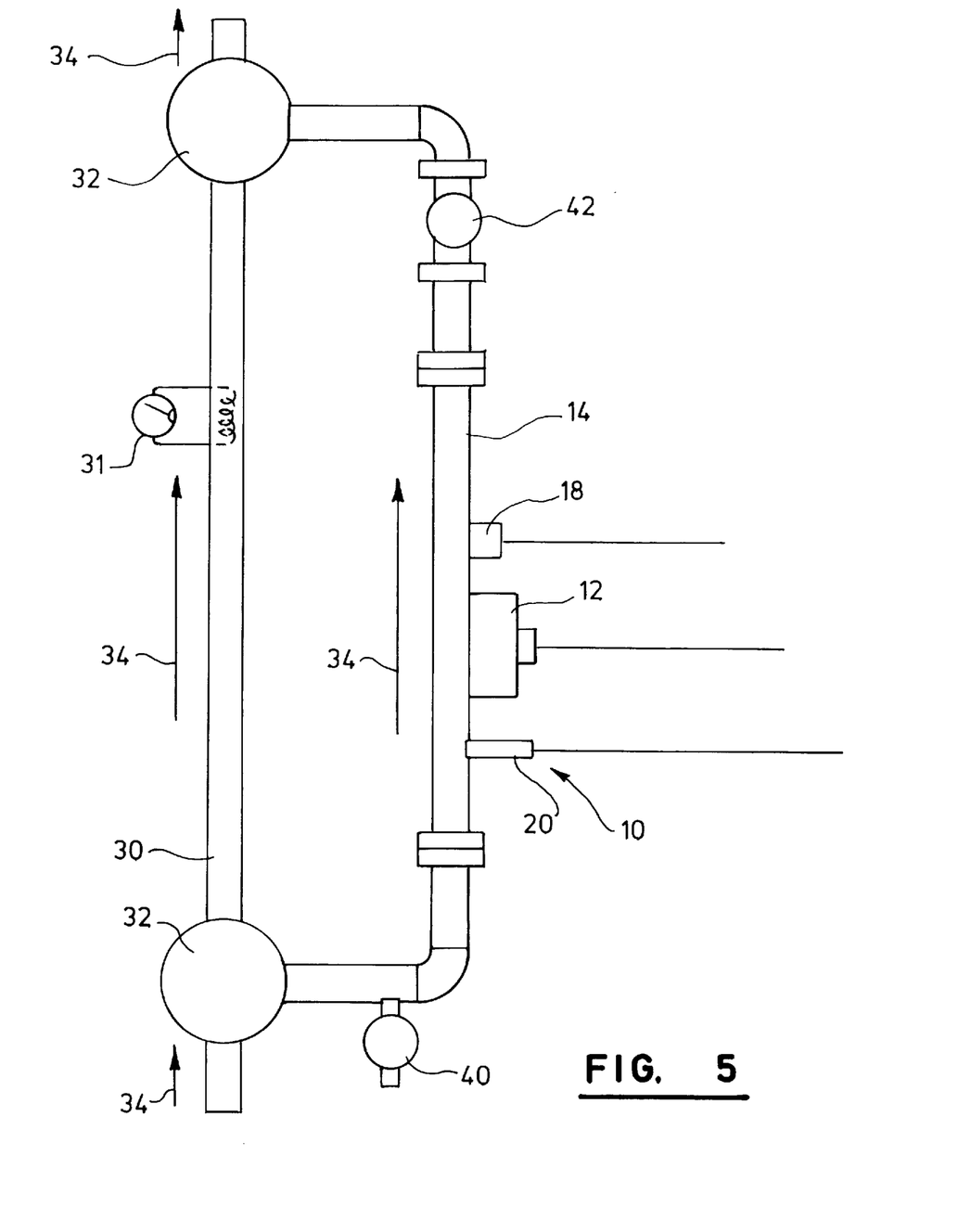
FIG. 5 is a schematic view of a gas sensing system of FIG. 1 connected to a continuous flow production pipe for a medium under consideration.

In the system shown in FIG. 5 the pipe 14 is a bypass to a main production flow pipeline 30 and 3-way isolation valves 32 are employed to optionally a) close flow to the bypass pipe 14, b) permit flow through both the main pipe 30 and the bypass pipe 14 or c) to direct the flow through the bypass pipe 14 only (depending on the required operational procedure). However, it will be appreciated that the gas sensing system could alternatively be fitted directly to the main pipe 32 if required. The direction of flow of the pipe contents are shown by the arrows 34. A conventional temperature sensor 31, such as one or more thermocouples, optionally may be included in pipe 32, as shown, to measure the temperature of the pipe contents.

A drain valve 40 and a flow restriction valve 42 are positioned on the bypass pipe 14 to permit, if required, the flow rate of the contents of the bypass pipeline 14 to be varied by operation of the appropriate valve. By closing valve 42 the flow rate may be decreased while opening valve 40 will enable the contents to be discharged. These valves 40 and 42 are not essential to the working of the gas sensing system.

The pressure transducer 18 is of conventional form while the pH sensor 20 may employ a standard pH Ion Sensitive Field Effect Transistor which is a rugged sensor designed for operation in extreme operating conditions. Both are well known and commonly available and, as such, will not be discussed further herein.

Figure 1:
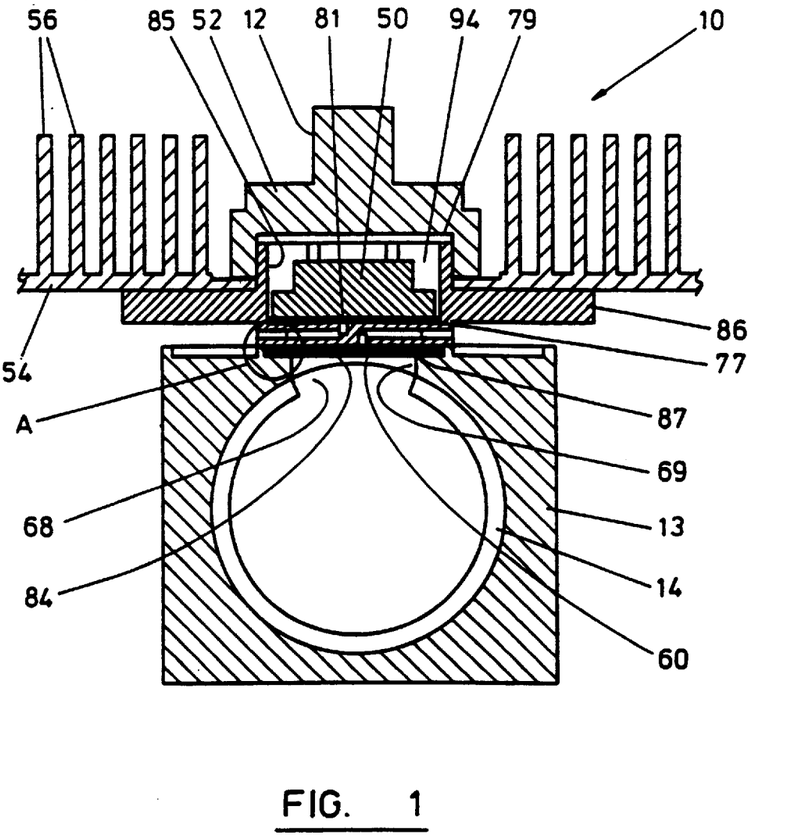
FIG. 1 is a cross sectional view of a gas sensing unit attached to a pipe of the system.

The system of the present example will be considered for detecting the concentration of sulphur dioxide ($SO_2$) in a preserve such as jam, sulphur dioxide being commonly employed as a preservative in those products from which the preserve is formed. $SO_2$ can also reside in food or other products as a result of natural production, steriliser residues from apparatus cleansing processes, residue from food bleaching processes or even from processes to modify the physical or mechanical characteristics of foodstuffs. However, it will be appreciated that it is desirable to know, whatever the source of the gas content in the product, the concentrations of such gases. With this in mind, the gas sensing unit 12 comprises a conventional and known sulphur dioxide (electrochemical) gas sensor 50 mounted in a stainless steel sensor housing 52. The sensor 50 (which may be that sold under the Trade Mark SIEGER) will usually comprise a potassium hydroxide gel which reacts with sulphur dioxide to provide an electrical output which is indicative of the sulphur dioxide concentration present. This sensor is capable of selectively detecting sulphur dioxide in the presence of other gasses. The gas sensitive sensor components are usually protected by a gas permeable sensor membrane (not shown). Such sensor technology is readily available and will not be discussed further herein.

Figure 2:
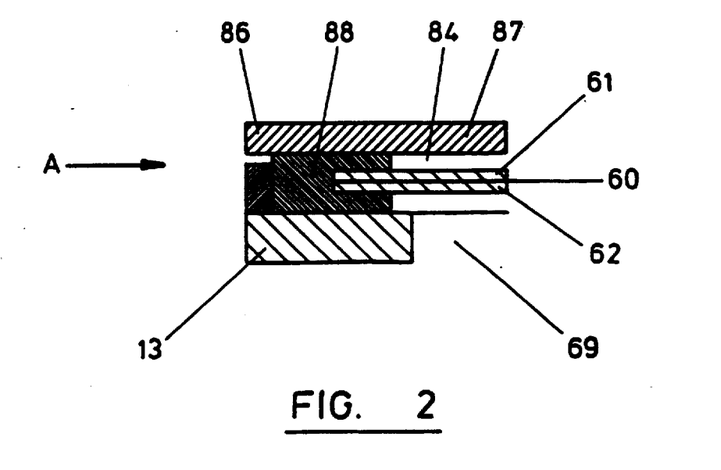
FIG. 2 is an enlarged view of the membrane support means indicated generally at A in FIG. 1.

The region of the pipe 14 on which the sensing unit 12 is mounted has an aperture 68 extending therethrough which is aligned with an aperture 69 in the mounting block 13, providing communication between the interior of the pipe 14 and the sensing unit 12. Mounted across the aperture 69 of the mounting block 13, in sealing engagement, is a gas permeable membrane 60 (permeable to sulphur dioxide gas) (FIG. 2 showing an enlarged view of part A of FIG. 1 show this membrane 60). This membrane 60 is supported on both faces thereof by sandwiching it between inner 61 and outer 62 stainless steel mesh retainer plates 64 which permit sulphur dioxide to pass therethrough and through the membrane 60. The membrane 60 is impermeable to the liquid contents of the pipe 14 while allowing sulphur dioxide gas therein to pass through. Such gas permeable membranes are well known and widely available, and the structure of such membranes may comprise a single layer or a multiplicity of layers. Known gas permeable membranes will also permit other gasses to pass through as well as sulphur dioxide but the sensor 50 employed within the system is capable of selectively detecting the sulphur dioxide gas within the chamber 84.

A nickel plated copper heat drain 86 has a recess 85 in which the sensor 50 is accommodated, and an upper aperture of this recess 85 is sealed with the sensor housing 52 to form an upper chamber 94, in which the sensor 50 is housed. This upper chamber 94 is effectively sealed by airtight silicon rubber gasket seals 77 and 79 which are respectively engaged between the sensor 50 and the heat drain 86 and the heat drain 86 and the sensor housing 52.

The seal 77 has an aperture 81 extending therethrough providing communication between the sensor 50 and a main, lower chamber 84. This lower chamber 84 is defined between the seal 77 (and sensor 50) and the gas permeable membrane 60. The heat drain 86 extends to define side walls of this second chamber 84 and has perforated arms 87 extending through the chamber 84 to increase the surface area of the heat drain exposed to a gas within the chamber to increase the heat dissipation away from such a gas. These arms to not restrict gas diffusion within the chamber 84. The heat drain 86 is retained clear of the membrane 60 by a silicon rubber (insulated) gasket seal 88, And this insulator 88 also serve to support the heat drain 86 clear of the mounting block 13 to prevent direct heating of the heat drain 86 by conduction from the mounting block 13 (such direct heat conduction from the pipe, though the mounting block to the heat drain could reduce the capability of the heat drain to conduct heat away from the gas within the chamber 84). This gasket seal 88 further serves to restrict heat conduction from the mounting block 13 to the unit 12. The heat drain 86 extends from the chamber 84 and is held in contact with a heat sink 54 which is mounted externally of the chamber 84 on the sensor housing 52 by the bolts 16 and 17. The heat sink 54 includes an array of heat dissipating fins or flanges 56 extending away from the housing 52 and which are intended to be simply cooled by the flow of air thereover. In addition, the heat sink also serves to cool the body of the gas sensing unit 12 by conducting heat away from the unit 12.

The insulated, annular and airtight seal 77 is also used to support the sensor 50 (which is connected to the sensor housing 52) in the chamber 94 clear of the heat sink 54 thus restricting heat conduction from the heat sink to the sensor 50, as well as defining the chamber 84 between this seal 77 and the membrane 60.

In practice, the bolts 17 pass through the sensor housing 52 and the heat sink 54 to engage the heat drain 84 and are tightened to compress these parts of the unit together, compressing the housing 52 against the upper seal 79. The bolts 16 pass through the heat sink 54 and the heat drain 86 to engage with the mounting block 13 to compress the unit 12 towards the mounting block 13 so that the heat drain 86 is held securely against the seal 88. The components carried by the bolts 16 and 17 can be slidably received thereon to allow the unit to be easily dismantled and the bolts 16 and 17 may then tightened to compress the components together against the respective seals 79 and 88 to form an airtight chambers 84 and 94.

Figure 8:
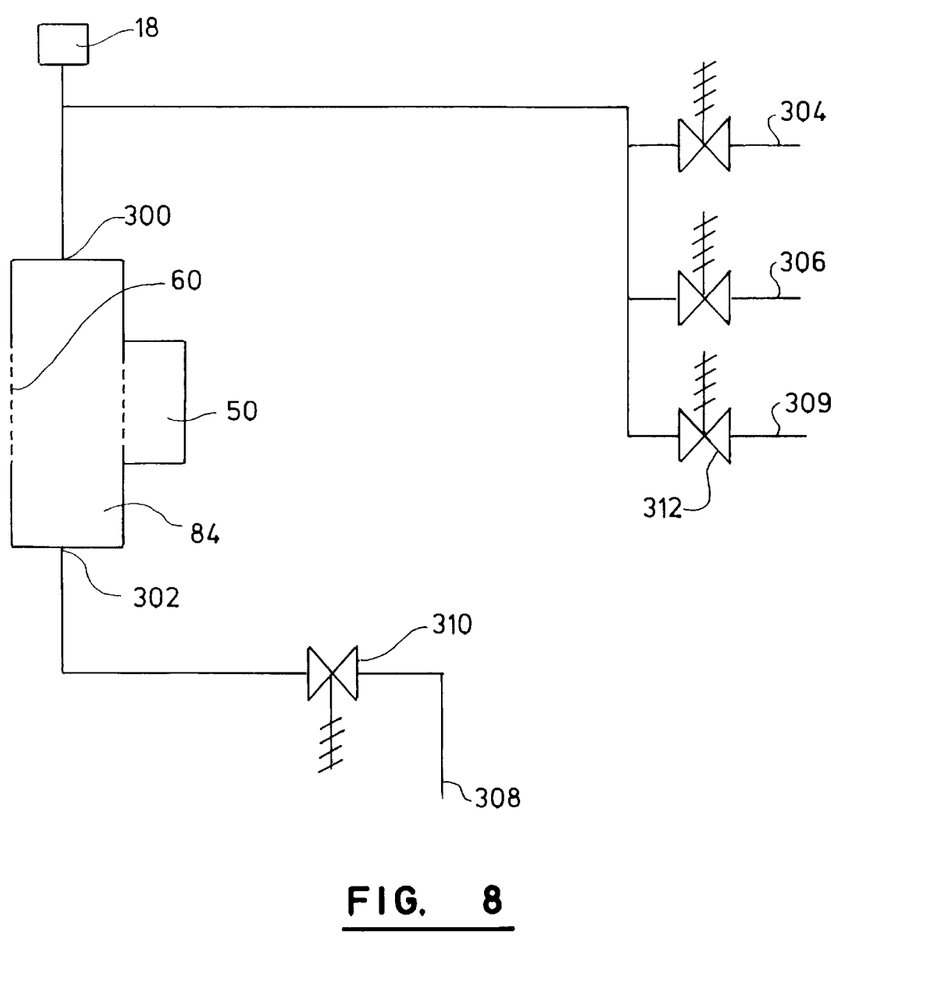
FIG. 8 is a schematic view of a purging system used in connection with the invention.

As shown in FIG. 8, provided with the chamber 84 are two gas ports 300, 302 each of which is connected by ducts to controlled valves 310, 312. One of these gas ports may be to a known pressurised gas supply 304, 306 (such as an inert gas, a control gas or air) whilst the other may be connected to a lower pressure system which may be atmosphere or a vacuum 308. By this arrangement, gaseous contents of the chamber 84 can be purged by opening the gas ports to positively charge the chamber 84 with an inert gas, or by a control gas of known concentration 309 for the purpose of calibrating the sensor 50. When the sensing system is to be used the chamber 84 is purged of sulphur dioxide and the two gas ports closed.

A primary use of the gas sensing system 10 is in the preserve manufacturing industry to detect the concentration of sulphur dioxide gas, in solution, in an unset (or molten) preserve prior to the bottling of the preserve. In such use, the pipe 14 is filled with the fluid (unset) preserve, which preserve will usually be at a high temperature, in excess of 85° C., for boiling off sulphur dioxide which is in solution in the preserve and which gas was initially used as a preservative for the ingredients in the preserve.

Sulphur dioxide forms weak complexes with certain naturally occurring organic materials in the preserve, particularly aldehydes and ketones. These complexes are stable at lower temperatures and are only broken down at temperatures greater than 60° C. Therefore, it is necessary to heat the preserve to a temperature of about 85° C. to break down these complexes in order to release the sulphur dioxide from the preserve.

Figure 6:
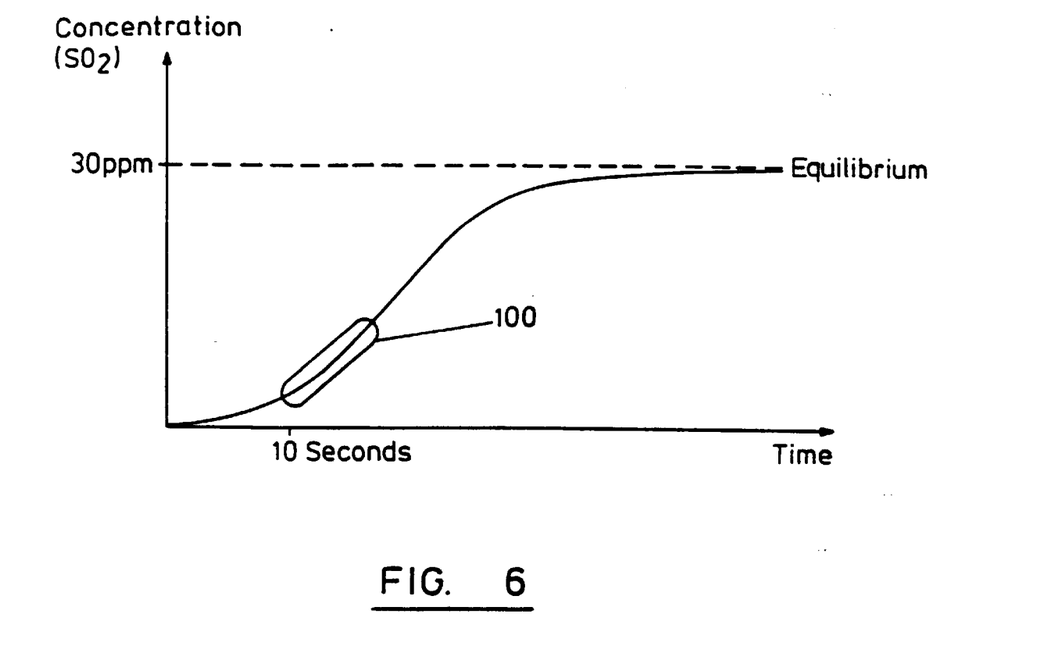
FIG. 6 is a graph showing the change of gas concentration, within the gas sensing unit of the system, with time.

As the preserve flows through the pipe 14 and the unit 10 at a temperature in excess of 85° C., sulphur dioxide gas in solution therein evolves and passes through the pipe aperture 68 and gas permeable membrane 60. The membrane 60 is impermeable to the preserve and the steel plates 61, 62 support the membrane 60 from mechanical stresses applied thereto by the preserve. The membrane 60 and plates 61, 62 will usually be made of a non-stick material or have a non-stick coating to alleviate fouling of the preserve on these parts. If the molten preserve is stationary within the pipe 14 the sulphur dioxide will evolve from solution in the preserve and pass through the membrane 60 until equilibrium is reached whereby the concentration of the sulphur dioxide within the cavity 84 is equal to the concentration of sulphur dioxide evolved from the preserve. This is shown in FIG. 6, showing the rise in sulphur dioxide concentration within the chamber 84 with time.

As the preserves are at a high temperature (of the order of 85° C. or greater) the sulphur dioxide gas evolved is also at this high temperature. However, known gas sensors 50 are recognised as having an operational temperature range up to 30°–45° C. and thus could not operate accurately and possibly be destroyed if subjected to the hot concentrations of sulphur dioxide gas and thereby raised above their temperature limit. Therefore, the hot sulphur dioxide gas which enters the chamber 84 has its physical characteristic of temperature controlled by passage through the heat drain 86, 87 which conducts excess heat from the gas in the chamber 84 to the heat sink 54 where it dissipates. Cool air is sometimes blown across the fins 56 of the heat sink to increase the heat dissipation. In this manner, the gas in the chamber 84, and the chamber itself, is cooled to a temperature below the maximum operational temperature of the gas sensor 50 before it passes through a sensor membrane of the sensor 50 for measurement. The aperture 81 of the seal 77 provides gaseous communication between the sensor components and the chamber 84. Additionally, the heat sink serves to conduct heat away from the body of the sensor 12 and the walls of the chamber 84 helping to cool the gas therein and alleviate conduction of heat to the sensor 50 which could also serve to raise the sensor temperature above its temperature operating range, and so helping maintain the sensor 50 temperature below its operational temperature limit.

The sensor 50 then provides an electrical output which is indicative of the concentration of the sulphur dioxide gas within the chamber 84 and, hence, in the preserve. In addition, the pH level of the preserve in the region of the sensor may be measured together with temperature and pressure of the preserve and, from a combination of this information and calibration measurements of the sensor, the true concentration of the sulphur dioxide gas in solution in the preserve may be determined.

The gas sensor 50 output is indicative of the gas concentration of the sample for given parameters of temperature, pH, pressure etc. This output may be calibrated by using complex, slow (but well known) testing techniques to accurately determine the gas content in such samples and comparing the accurate results with the sensor output and determining how such measurements and sensor outputs vary for different operating conditions (and product). Such known techniques for determining the absolute concentrations of the gas content in a product sample will include mass spectrometry using gas chromatography, liquid chromatography, pyrolysis analysis and cryogenic refocussing techniques or liquid and ion chromatography techniques. Once the system 10 has been calibrated by this method then the gas concentrations within the tested product may be determined from the sensor output and operating conditions.

By use of the aforementioned procedure, on line gas concentration measurements can be taken with the results being made available with little delay. An obvious benefit of this is that the acceptability of the preserve can be determined rapidly and, should the sulphur dioxide gas concentration exceed an acceptable level, appropriate steps can be taken quickly to remedy the situation without incurring a large loss in preserve production.

The foregoing description of the system 10 considers its use with a sample of the preserve being directed into the bypass pipe 14 and retained for stationary testing. However, an alternative use of the system 10 may be employed for the continuous measurement of the sulphur dioxide gas concentration with the preserve in a continually flowing state. In such a case, the gas sensing system 10 is connected directly to the main production pipe 30. Preferably, however, the sensing system 10 is connected in parallel to the bypass pipe 14 as previously described, but in this situation the preserve is allowed to flow over the membrane 60 during the measurement procedure. This arrangement allows for maintenance of the sensor unit 12 without the need to halt production by simply sealing off the by-pass pipe from the main production pipe 30.

In either of the applications of the system 10 to a continuous flow measurement arrangement as described, the preserve is again at a temperature in excess of 85° C. so that the sulphur dioxide that evolves from the preserve will diffuse through the membrane 60 in an effort for the gas to reach equilibrium across that membrane 60. In one such scenario, once equilibrium is reached the concentration of sulphur dioxide in the chamber 84 will only vary when the concentration of gas within the preserve varies and causes diffusion of the sulphur dioxide across the membrane 60 in either direction in an effort to maintain equilibrium. Measurements from the sensor 50 can thus be monitored for fluctuations to indicate any possible variations in the gas concentration of the product.

However, it is preferred that a more sophisticated use of the gas sensing system 10 is employed to detect the concentration of sulphur dioxide in a continuous preserve flow. It is possible that the flow rate of the preserve may be such that where a portion of the preserve has a concentration of sulphur dioxide higher than a normal, or acceptable level, it will take some time for equilibrium indicative of the higher level concentration to be reached (due to the rate of diffusion slowing down as equilibrium is approached) and thus the change in concentration may not be detected as rapidly as is desirable. To alleviate this inconvenience, a succession of independent gas concentration measurements can be taken intermittently and continuously using apparatus similar to that previously described. FIG. 6 shows a graph of the increase in concentration of sulphur dioxide within the cavity 84 for testing a stationary sample of the preserve (as previously described) where the increase in concentration within the chamber 84 will follow a recognised pattern, in which the concentration initially increases at a high rate and subsequently increases at a progressively slower rate as the concentration approaches equilibrium across the membrane 60 after several minutes. However, by the use of standard mathematical extrapolation principles, it is possible to determine the final equilibrium gas concentration from a study of the initial slope of the graph as shown at region 100 in FIG. 6 after about 10–15 seconds. Thus, the sensing system 10 can be employed to take successive gas concentration measurements, each over an initial period of 10 to 15 seconds from the initiation of the gas diffusing into the chamber 84 in an effort to reach equilibrium (across the membrane 60) after purging the chamber 84. From these results, successive equilibrium concentrations of the preserve can be mathematically determined. This obviously offers the benefit of determining the gas concentration in a much quicker fashion, normally in under twenty seconds compared to several minutes normally required for equilibrium to be reached.

To take advantage of the aforementioned principle using successive measurements, it is possible that the basic gas sensing system 10 will need to be modified slightly. The normal gas concentrations of sulphur dioxide within the molten preserve is expected to be less than 30 parts per million (ppm) (although this may be exceeded when the product is defective) and as such the gas sensor 50 would normally be required to operate efficiently up to a sulphur dioxide concentration greater than 30 ppm. However, for the modified use of the system 10, a more sensitive sensor 50 is preferred for rapidly and accurately determining the initial increase in gas concentration before equilibrium is reached and for this a sensor 50 may be employed having a range up to, say, 10 ppm which permits rapid and accurate readings to be made up to that low concentration. With such a modification it is therefore necessary to prevent the concentration within the chamber 84 from exceeding the sensor limitation of, say, 10 ppm (otherwise it may be that the sensor will "burn out"). With this in mind, the chamber 84 is purged of the sulphur dioxide periodically (say every 15 seconds) before its concentration in the chamber 84 develops to an extent greater than that recommended or permitted for the sensor 50. This purging and effective control in the physical characteristics of the sulphur dioxide in the chamber is achieved by blowing air or an inert gas through one of the gas ports (not shown) which are provided in the chamber 84, and purging the mixed gases by way of the second gas port prior to the sulphur dioxide concentration in the chamber 84 exceeding that recommended or permitted for the sensor 50.

Figure 7:
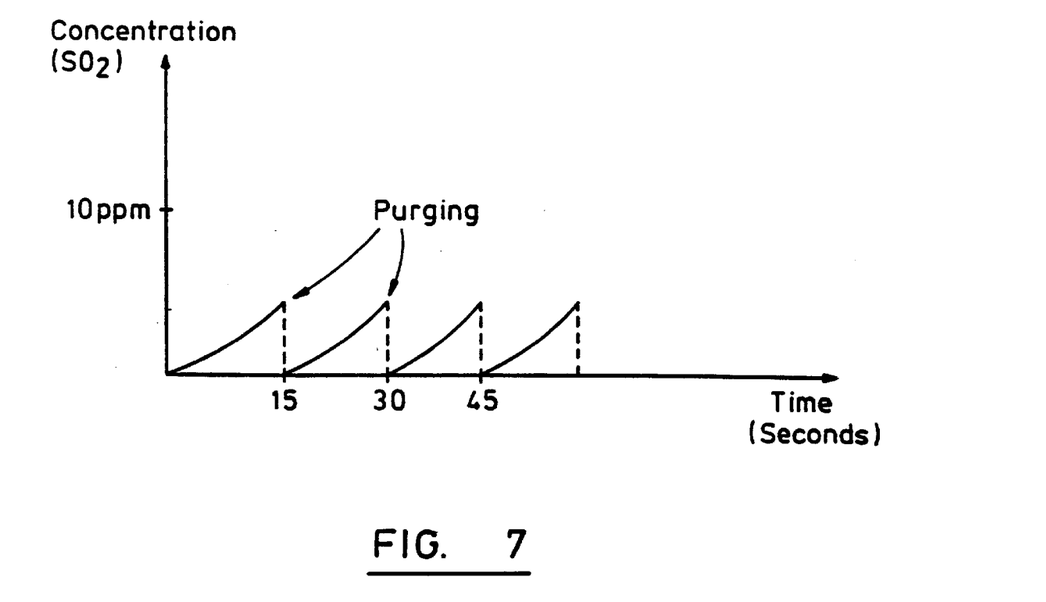
FIG. 7 is a graph of gas concentration, within the gas sensing unit of the system, with time and in which system a gas purging operation is employed.

Following each purging stage the two gas ports are closed whilst sulphur dioxide gas in the preserve continues to diffuse through the membrane 60 and the initial sulphur dioxide gas concentration level increase in chamber 84 is measured. At the same time pH measurements and temperature measurements of the preserve in the pipe will likely be taken for use in calculating the sulphur dioxide concentration in the preserve. The pressure of the preserve within the pipe may also be measured if required. The flow rate of the preserve through the pipe will likely be such that the gas concentration in the preserve will not vary greatly during each (approximately) 15 second measurement time so that an accurate measurement of the gas concentration within the preserve may be expected. Furthermore, by repeating the purging/measurement process intermittently (see FIG. 7 for a graphical indication of the sulphur dioxide concentration in the cavity 84 during this process of measuring/purging) any variations in the sulphur dioxide concentration can be detected extremely quickly and any necessary alterations to the manufacturing process can be effected immediately.

In either of the two uses described, the accuracy of the system is increased at higher temperatures of the preserve since a higher proportion of the sulphur dioxide is evolved from the preserve, thus enhancing the system sensitivity. However, although heating preserves has no adverse effect on the final product, in certain other products, for example wine, the quality of the final product will be adversely affected by heat. Therefore, a feature of this invention is that gas measurements emanating from the product can be measured at a wide range of temperatures. For example, in wine production a series of sulphur dioxide measurements may be taken with the wine at a temperature above 60° C. using the present system to obtain a series of calibration results and similar measurements taken at temperatures well below 60° C. From these two sets of results the relationship between the true sulphur dioxide content and the sulphur dioxide content at an ambient temperature can be determined, allowing a non-destructive test on the majority of the product. The relationship between true gas content and the gas content measured at lower temperatures will vary for different materials, but the present system allows for high temperature measurements to be made and such readings used to calibrate the lower temperature readings. Thus the gas sensing system herein described can also be used for calibration of gas measurements at lower temperatures.

It has also been found that by stirring or otherwise agitating the product to produce turbulent flow in the pipe 14 in the region of the sensing unit 12 helps to promote the expulsion of $SO_2$ from the product. This assists the measurement process since for calibrated agitation techniques more $SO_2$ is evolved and the higher gas concentrations within the unit 12 are more readily measured. However, in using such agitation techniques it will be appreciated that accurate control measurements of the sample will also be required to determine accurately the gas concentrations within the sample and to calibrate the sensor 50 measurements accordingly to take into account the controlled agitation techniques.

The sensing system 10 can ultimately be used to automate the production of the preserve. For example, the system 10 may be connected directly to a computer control system which analyses the sensor 50 results to calculate the gas concentrations within the preserve and, should the concentration levels rise beyond a predetermined concentration the control system could automatically divert the unacceptable preserve from, say, a bottling line whilst simultaneously adjusting the heating of the preserve to increase the rate of "boiling off" of the sulphur dioxide—thereby ensuring that unacceptable preserve is not made available for consumption and rapidly correcting the problem of excess sulphur dioxide concentration to ensure minimum product wastage.

The gas sensor may be regularly calibrated using test samples (of known concentrations) of sulphur dioxide injected directly into the chamber 84 through one of its ports (not shown) to ensure that the system output accurately reflects the gas concentrations within the sensor unit chamber 84.

An additional advantage of the present invention is the ease of replacement of the sensor 50 if it becomes damaged by simply dismantling the system 10 and replacing the damaged or worn parts.

Although we have discussed sensor systems here which monitor the temperature and pressure of the product (whether stationary or moving) within the pipe 13, temperature and pressure sensors may also be inserted within the chamber 84 of the sensor unit 12 for measuring the temperature and pressure within the chamber. Such measurements may be used to further calibrate the sensor system 10 and may also prove useful in detecting failure of the gas permeable membrane 60 by any sudden internal pressure or temperature variations. In production models of the present invention it has also proved useful to include liquid drain valves in the chamber 84 design to allow the removal of any condensate which may build up over prolonged use.

Figure 4:
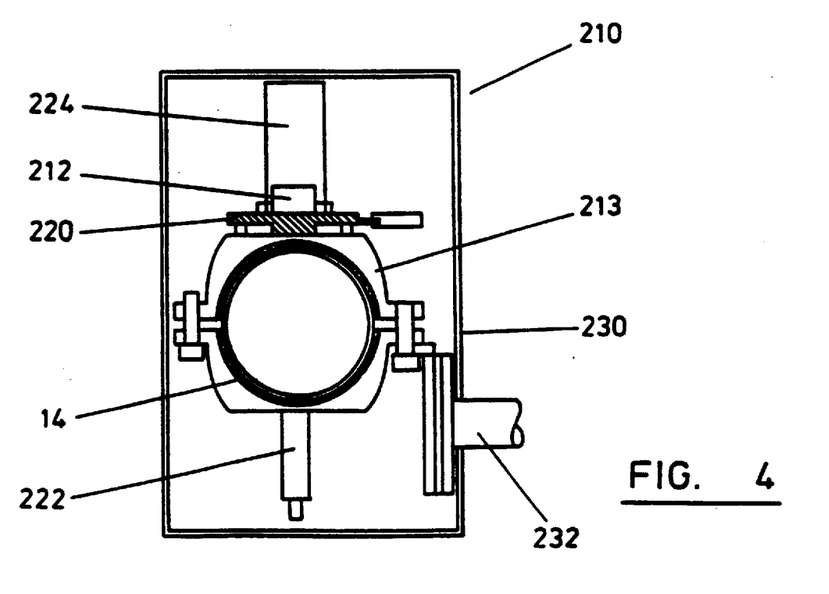
FIG. 4 is a cross sectional view of a second embodiment of a gas sensing unit.

Further embodiments of the present invention may utilize other methods of cooling the gas within the chamber 84 (and the body of the system 12 and the sensor 50), such as an array of water/fluid cooled pipes within the chamber or the use of a water jacket surrounding the chamber to withdraw heat from the gas before the sensor 50 is exposed to it. Alternatively, a Peltier cooling device may be employed within the chamber 84 to withdraw heat from any gas therein. FIG. 4 shows such a further embodiment of a gas sensing system 10 comprising a more compact array of sensors than shown in FIG. 5 and employing a water cooled sensor unit. FIG. 4 shows a gas sensing system 210 comprising a mounting block 213 mounted about a pipe 14. A gas sensing unit 212 of similar construction to unit 12 of the first embodiment in FIG. 1 is mounted on the mounting block and in gaseous communication, via a gas permeable membrane (not shown) with the pipe 14 contents. However, the heat drain of this unit 212 is connected to a water cooled jacket 220. In addition a pH sensor 222 and a pressure sensor 224 (for measuring the product pH and pressure, respectively, in the pipe 14) are both affixed to the mounting block 213. Temperature probes, such as thermocouples or platinum resistance thermometers, are also inserted into the pipe 213 in this region for determining the product temperature. The system 10 is then enclosed within a wire frame cover 230 to protect the pH, gas, pressure and temperature sensors (and the electrical outputs thereof) of the system from atmospheric interference which could adversely affect such readings. These shielded sensor outputs may then be fed, by shielded cables 232, to the appropriate monitors to measure the gas concentrations in the sensor 212, and temperature, pressure and pH levels of the product, and this data interpreted as previously discussed with reference to the system 10.

It will be appreciated that the present invention is not limited to use in the preserve manufacturing industry or even to the food and drink industry and may be used with advantage in a large number of situations whereby it is necessary to determine the gas (not necessarily sulphur dioxide) content of a flowable medium. A particular application may be in the wine industry again to determine the concentration of sulphur dioxide in a wine; in this use however, it may not be necessary to cool the gas within the chamber (since the wine need not be hot). It is also envisaged that this invention will have wide application in the production, and control, of fruit juices, fruit based beverages and fruit syrups.

It should further be appreciated that the present invention is not restricted to the determination of sulphur dioxide concentrations and, by use of different gas sensors, the gas sensing system can be applied for determining the concentration of an appropriate gas. If required, the sensor system 10 can be adapted to be simply immersed within the flowable medium.

We claim:

1. A gas sensing system for the detection of gas concentrations emanating from a flowable medium which comprises a membrane structure permeable to said gas and disposed between said flowable material and a chamber, said membrane structure being impervious to said flowable material; a gas sensor exposed to said chamber for the detection of concentration of said gas therein, wherein the gas sensor has an operational temperature limitation less than a predetermined temperature, wherein temperature control means are provided in the chamber for withdrawing heat from the chamber and said gas to reduce the gas temperature within the chamber to below the predetermined temperature.

2. A system as claimed in claim 1 in which the temperature control means comprises a heat sink having a heat conductive member within the chamber connected to heat conducting fins outside the chamber, in which heat is conducted away from the chamber by the fins.

3. A system as claimed in claim 1 in which the sensor has an operational concentration detection limitation less than a predetermined concentration in order to provide increased detection accuracy, and wherein purging means is provided to reduce the concentration of gas within the chamber, when necessary, to below the predetermined concentration.

4. A system as claimed in claim 3 in which the chamber is sealed and purging means comprises at least two ducts, at least one duct to allow the controlled introduction of a control gas into the chamber and at least one second duct for allowing gas to be removed from the chamber.

5. A system as claimed in claim 1 which further comprises a pH sensor for detecting the pH level of the flowable medium.

6. A system as claimed in claim 5 in which the pH sensor comprises a pH Ion Sensitive Field Effect Transistor sensor.

7. A system as claimed in claim 1 which further comprises pressure detection means for determining the pressure of the flowable medium.

8. A system as claimed in claim 1 comprising a temperature detection means for determining the temperature of the flowable medium.

9. A system as claimed in claim 1 in which the flowable medium flows through a pipe and the membrane structure is situated in a wall of said pipe such that a side of the membrane structure, directed inwards towards a central axis of the pipe, is at least partially immersed in the flowable medium.

10. A system as claimed in claim 9 in which the membrane structure is supported by a rigid lattice frame to increase its strength.

11. A system as claimed in claim 1 in which the gas sensor is a electrochemical sulphur dioxide detector and the membrane means is permeable to sulphur dioxide.

12. A system as claimed in claim 1 in which said membrane structure comprises a single layer or a multiplicity of two or more layers.

13. A method of determining the concentration of the gas emanating from a flowable medium using a gas sensor, comprising the steps of separating and isolating the gas from the flowable medium and adjusting the physical characteristics of the said isolated gas in order that the gas is compatible with the predetermined operating ranges of the sensor; whereby the gas is separated from the flowable medium by placing a membrane structure that is permeable to the gas and impermeable to the flowable medium between the flowable medium and an isolated chamber to allow the gas to defuse into the isolated chamber; and where the sensor has an operational temperature limitation less than a predetermined temperature whereby heat is withdrawn from the isolated gas according to temperature control means provided within the isolated chamber to reduce the temperature of the gas to below the predetermined temperature.

14. A method as claimed in claim 13 in which the sensor has an operational concentration detection limitation less than a predetermined concentration whereby the concentration of the isolated gas is prevented from reaching the predetermined concentration.

15. A method as claimed in claim 14 in which the increase in concentration of the isolated gas is measured against time as the said gas diffuses through a membrane structure in an effort to reach an equilibrium and the equilibrium concentration of the gas is calculated from the rate of increase of gas concentration before equilibrium is reached and the chamber is purged of the gas before the gas concentration reaches the predetermined concentration.

* * * * *